(12) United States Patent
Kesenheimer et al.

(10) Patent No.: US 9,796,730 B2
(45) Date of Patent: Oct. 24, 2017

(54) HALOGENATED BENZOXAZINES AND THEIR USE

(71) Applicant: Eberhard Karls Universitaet Tuebingen Medizinische Fakultaet, Tuebingen (DE)

(72) Inventors: Christian Kesenheimer, Dusslingen (DE); Florian Maier, Reutlingen-Oststadt (DE); Ramona Stumm, Sonnenbuehl (DE); Bernd Pichler, Scheyern (DE)

(73) Assignee: EBERHARD KARLS UNIVERSITAET TUEBINGEN MEDIZINISCHE FAKULTAET, Tuebingen (DE)

( * ) Notice: Subject to any disclaimer, the term of this patent is extended or adjusted under 35 U.S.C. 154(b) by 51 days.

(21) Appl. No.: 14/632,534

(22) Filed: Feb. 26, 2015

(65) Prior Publication Data

US 2015/0166572 A1   Jun. 18, 2015

Related U.S. Application Data

(63) Continuation of application No. PCT/EP2012/067006, filed on Aug. 31, 2012, which is a continuation of application No. PCT/EP2012/066713, filed on Aug. 28, 2012.

(51) Int. Cl.
*A61K 51/04* (2006.01)
*C07D 498/14* (2006.01)

(52) U.S. Cl.
CPC ........ *C07D 498/14* (2013.01); *A61K 51/0463* (2013.01)

(58) Field of Classification Search
CPC .............................. A61K 49/00; A61K 51/04
See application file for complete search history.

(56) References Cited

U.S. PATENT DOCUMENTS

2011/0208064 A1* 8/2011 Chongzhao ........ A61K 49/0021
600/476

FOREIGN PATENT DOCUMENTS

| EP | 1193260 A1 | 3/2002 |
|---|---|---|
| WO | 0216333 A2 | 2/2002 |
| WO | 2004083195 A1 | 9/2004 |
| WO | 2005016934 A1 | 2/2005 |
| WO | WO2005016934 * | 2/2005 |
| WO | 2014032732 A1 | 3/2014 |

OTHER PUBLICATIONS

Koenig, K.H. "Zur Thermochromie und Konstitution unsymmetrischer [Hydroxy-alkylamino]-p-benzochinone, I Synthese, Eigenschaften und Konstitutionsabhangigkeit von Derivaten des p-Benzochinons", Chemische Berichte, vol. 92 (No. 2), Feb. 1959:257-267.
Berlin, A.Y. "Some Reactions of B, B'-Dihydroxydiethylamino-p-benzoquinone", J. Org. Chem. USSR, 1958:2390-2394.
Berlin, A.Y. "Some Reactions of B, B'-Dihydroxydiethylamino-p-benzoquinone", J. Org. Chem. USSR, 1958:2355-2359 English translation of Berlin, A.Y. "Some Reactions of B, B'-Dihydroxydiethylamino-p-benzoquinone", J. Org. Chem. USSR, 1958:2390-2394, disclosed here.
Hintersteiner, M. et al., "In vivo detection of amyloid-B deposits by near-infrared imaging using an oxazine-derivative probe", Nature Biotechnology, vol. 23 (No. 5), May 2005:577-583.
PCT Search Report related to Int'l App. No. PCT/EP2012/067006, mailed Apr. 19, 2013, citations listed above (10 pgs.).
English translation of PCT Search Report related to Int'l App. No. PCT/EP2012/067006, mailed Apr. 19, 2013, citations listed above (2 pgs.).
English translation of Written Opinion related to Int'l App. No. PCT/EP2012/067006, mailed Apr. 19, 2013 (7 pgs.).

* cited by examiner

*Primary Examiner* — Michael G Hartley
*Assistant Examiner* — Jagadishwar Samala
(74) *Attorney, Agent, or Firm* — Loeb & Loeb LLP

(57) ABSTRACT

The present invention relates to novel halogenated benzoxazines, methods for their production, their use for the diagnosis of diseases and their use for the production of medicaments for the diagnosis of diseases, preferably dementia diseases and in particular the Alzheimer's disease, in humans and/or animals.

15 Claims, 4 Drawing Sheets

HALOGENATED BENZOXAZINES AND THEIR USE

CROSS-REFERENCE TO RELATED APPLICATIONS

This application is a continuation of copending international patent application PCT/EP2012/067006 filed on 31 Aug. 2012 and designating the U.S., which has been published in German and claims priority from international patent application PCT/EP2012/066713. The entire contents of these prior applications are incorporated herein by reference.

FIELD OF THE INVENTION

The present invention relates to novel halogenated benzoxazines, methods for their production, their use for the diagnosis of diseases and their use for the production of medicaments for the diagnosis of diseases, preferably dementia diseases and in particular the Alzheimer's disease in humans and/or animals.

BACKGROUND OF THE INVENTION

Related Prior Art

In an aging community the diagnosis and therapy of diseases which usually only appear in the elderly becomes more and more important. To such diseases belong, amongst others, the neurodegenerative diseases and in particular the Alzheimer's disease, which represents about 70% of all neurodegenerative diseases.

The Alzheimer's disease is a neurodegenerative disease characterized by an increasing worsening of the cognitive performance, dementia and the loss of memory capabilities. On the cellular level the Alzheimer's disease is characterized by the formation of plaques of beta amyloid peptides (Aβ plaques) which can be formed already many years before the appearance of clinical symptoms.

A problem in the diagnosis and in extenso the therapy of the Alzheimer's disease and in the development of effective therapies for the Alzheimer's disease is that until this day a final diagnosis is only possible in the context of an autopsy by staining the Aβ plaques. The possibility to detect the Aβ plaques in the living organism is therefore of particular interest since the formation of the Aβ plaques starts significantly before the outbreak of the clinical symptoms and, consequently, with such a detection a significantly earlier identification and therapy of the Alzheimer's disease would be possible.

There are already several approaches to label and visualize the Aβ plaques. In the WO 2005/016934 compounds are described which are structurally similar to the present compounds and which are described as fluorescent dyes for the Aβ plaques. However it has been shown for such compounds that they are not suitable for the diagnostics of Alzheimer in humans since its fluorescence cannot be monitored through the human scull, i.e. in the living human.

Another approach in the research on the diagnostics of Alzheimer is the development of labeled tracer compounds, in particular radioactively labeled tracer compounds, for a use in non-invasive detection methods such as the positron emission tomography (PET) or the magnetic resonance tomography (MRT). The currently most promising compounds in this field are thioflavin derivatives whereas the most developed compound is a radiolabeled thioflavin derivative designated as Pittsburgh Compound B (PIB). Compounds of such kind are e.g. described in the WO 02/16333 and the WO 2004/083195. These compounds, however, have the disadvantage that at a certain concentration at the Aβ plaques they show a saturation effect, that is to say that despite an increase of the amount at the Aβ plaques no increase in the tracer signal can be identified. Furthermore, with these compounds Aβ plaques deposed at vessels cannot be detected. In view of these disadvantages, these compounds are appropriate for a general diagnosis, however it is doubtful whether the course of the disease can be monitored in a reliable manner.

Therefore, there is an urgent need for novel compounds for a use in the diagnostics of Alzheimer, which do not comprise the above-mentioned disadvantages and by means of which the Alzheimer's disease can be diagnosed in vivo at an early stage and can be monitored throughout the entire course of disease.

SUMMARY OF THE INVENTION

Surprisingly it has been found that the halogenized benzoxazines described in the present invention are suitable as tracers for the Aβ plaques, e.g. for the PET and MRT. In particular, it has been shown that these compounds provide a signal over a broad concentration range that correlates with the concentration of the Aβ plaques.

A subject matter of the invention are compounds of the formula

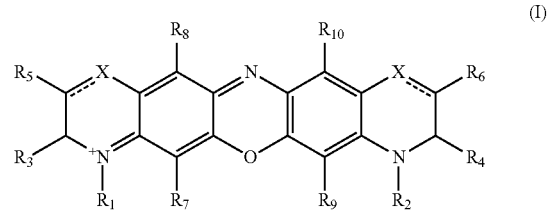

(I)

in which,
X and Y independently from one another represent CH, $CH_2$, N, S or O,
wherein X and Y are not simultaneously CH or $CH_2$,
wherein, if X represents CH or N, the dotted line between X and the neighboring atom represents a bond, and
wherein, if Y represents CH or N, the dotted line between Y and the neighboring atom represents a bond,
$R_1$ and $R_2$ independently from one another are selected from the group consisting of $(C_1$-$C_2)$-alkyl, $(C_1$-$C_2)$-alkoxy and $(C_1$-$C_2)$-alkyl sulfonyl,
wherein alkyl, alkoxy and alkyl sulfonyl can be substituted with one up to three substituents selected from the group consisting of $^{76}Br$, $^{75}Br$, $^{19}F$ and $^{18}F$,
$R_3$, $R_4$, $R_7$, $R_8$, $R_9$ and $R_{10}$ independently from one another are selected from the group consisting of hydrogen, halogen, hydroxy, amino, cyano, nitro, $(C_1$-$C_4)$-alkyl, $(C_1$-$C_4)$-alkyl amino and $(C_1$-$C_4)$-alkoxy,
wherein alkyl and alkoxy can be substituted with one up to three substituents selected from group consisting of $^{76}Br$, $^{75}Br$, $^{19}F$ and $^{18}F$,
$R_5$, if X represents CH or N, represents a substituent selected from the group consisting of hydrogen, halogen, hydroxy, amino, cyano, nitro, $(C_1-C_4)$-alkyl, $(C_1-C_4)$-alkyl amino and $(C_1-C_4)$-alkoxy,
  wherein alkyl and alkoxy can be substituted with one up to three substituents selected from group consisting of $^{76}Br$, $^{75}Br$, $^{19}F$ and $^{18}F$,
$R_5$, if X represents $CH_2$, S or O, represents two substituents independently from one another are selected from the group consisting of hydrogen, halogen, hydroxy, amino, cyano, nitro, $(C_1-C_4)$-alkyl, $(C_1-C_4)$-alkyl amino and $(C_1-C_4)$-alkoxy,
  wherein alkyl and alkoxy can be substituted with one up to three substituents selected from group consisting of $^{76}Br$, $^{75}Br$, $^{19}F$ and $^{18}F$,
$R_6$, if X represents CH or N, represents a substituent selected from the group consisting of hydrogen, halogen, hydroxy, amino, cyano, nitro, $(C_1-C_4)$-alkyl, $(C_1-C_4)$-alkyl amino and $(C_1-C_4)$-alkoxy,
  wherein alkyl and alkoxy can be substituted with one up to three substituents selected from group consisting of $^{76}Br$, $^{75}Br$, $^{19}F$ and $^{18}F$,
$R_6$, if Y represents $CH_2$, S or O, represents two substituents independently from one another are selected from the group consisting of hydrogen, halogen, hydroxy, amino, cyano, nitro, $(C_1-C_4)$-alkyl, $(C_1-C_4)$-alkyl amino and $(C_1-C_4)$-alkoxy,
  wherein alkyl and alkoxy can be substituted with one up to three substituents selected from group consisting of $^{76}Br$, $^{75}Br$, $^{19}F$ and $^{18}F$,
wherein the compound of the formula (I) comprises at least one substituent selected from the group consisting of $^{76}Br$, $^{75}Br$, $^{19}F$ and $^{18}F$,
and the salts thereof, the solvates thereof and the solvates of the salts thereof.

Compounds according to the invention are the compounds of the formula (I) and the salts thereof, the solvates thereof and the solvates of the salts thereof, and the compounds of the following embodiment(s) encompassed by the formula (I), and the salts thereof, solvates thereof and the solvates of the salts thereof, as far as the compounds mentioned in the following which are encompassed by the formula (I) are not already salts, solvates and solvates of the salts.

In case the compounds according to the invention can exist in tautomeric forms, the present invention encompasses all of the tautomeric forms.

The salts in the context of the present invention are preferred as physiologically harmless salts of the compounds according to the invention. However, also encompassed are salts which are itself not suitable for pharmaceutical applications, however can e.g. be used for the isolation or purification of the compounds according to the invention.

Physiologically harmless salts of the compounds according to the invention preferably comprise acid addition salts of mineral acids, carbon acids and sulfonic acids, e.g. salts of the hydrochloric acid, bromhydric acid, sulfuric acid, phosphoric acid, methane sulfonic acid, ethane sulfonic acid, toluene sulfonic acid, benzene sulfonic acid, naphthalene sulfonic acid, acetic acid, trifluoroacetic acid, propionic acid, lactic acid, tartaric acid, malic acid, citric acid, fumaric acid, maleic acid, and benzoic acid.

For the purposes of the invention solvates refer to those forms of the compounds according to the invention which form in a solid or liquid state a complex by coordination with solvent molecules. Hydrates are a specific form of solvates in which the coordination takes place with water.

In the context of the present invention the substituents have the following meaning, unless specified otherwise:

Alkyl and the alkyl parts in alkoxy and alkyl sulfonyl refer to a straight or branched alkyl and encompasses, unless indicated otherwise, $(C_1-C_6)$-alkyl, in particular $(C_1-C_4)$-alkyl, such as e.g. methyl, ethyl, n-propyl, isopropyl, n-butyl, isobutyl, tert-butyl.

In the context of the invention alkoxy preferably refers to a straight or branched alkoxy residue, in particular with 1 to 6, 1 to 4 or 1 to 3 carbon atoms. Preferred is a straight or branched alkoxy residue with 1 to 3 carbon atoms. By the way of an example and preferably the following are mentioned: methoxy, ethoxy, n-propoxy, iso-propoxy, t-butoxy, n-pentoxy and n-hexoxy.

Alkyl amino refers to an alkyl amino residue with one or two (independently from one another selected) alkyl substituents, by the way of an example and preferably for methyl amino, ethyl amino, n-propyl amino, isopropyl amino, tert-butyl amino, n-pentyl amino, n-hexyl amino, N,N-dimethyl amino, N,N-diethyl amino, N-ethyl-N-ethyl amino, N-methyl-N-n-propyl amino, N-isopropyl-N-n-propyl amino, N-tert-butyl-N-methyl amino, N-ethyl-N-n-pentyl amino and N-n-hexyl-N-methyl amino. $C_1-C_3$-alkyl amino for example refers to a monoalkyl amino residue with 1 to 3 carbon atoms or for a dialkyl amino residue with 1 to 3 carbon atoms per each alkyl substituent.

Halogen refers to fluorine, chlorine, bromine or iodine and their isotopes, wherein fluorine and bromine are preferred, unless specified otherwise. In particular in the context of the invention halogen can be $^{76}Br$, $^{75}Br$, $^{19}F$ and $^{18}F$.

The above-mentioned general definitions of the residues or those of the preferred ranges both apply to the final products of the formula (I) as well as in each case correspondingly to the starting materials or intermediate products required for the production.

The definitions of the residues individually indicated in the respective combinations or preferred combinations of residues are—independently from the respectively indicated combinations of the residues—arbitrarily replaced by the residue definitions of other combinations.

Another subject matter of the invention are compounds of the formula (I), in which
  X and Y independently from one another represent CH, $CH_2$, N, S or O,
    wherein X and Y are not simultaneously CH or $CH_2$,
    wherein, if X represents CH or N, the dotted line between X and the neighboring atom, represents a bond, and
    wherein, if Y represents CH or N, the dotted line between Y and the neighboring atom represents a bond,
  $R_1$ and $R_2$ independently from one another are selected from the group consisting of $(C_1-C_2)$-alkyl, $(C_1-C_2)$-alkoxy and $(C_1-C_2)$-alkyl sulfonyl,
    wherein alkyl, alkoxy and alkyl sulfonyl can be substituted with one up to three substituents selected from the group consisting of $^{76}Br$, $^{75}Br$, $^{19}F$ und $^{18}F$,
  $R_3$, $R_4$, $R_7$, $R_8$, $R_9$ and $R_{10}$ independently from one another are selected from the group consisting of hydrogen, halogen, hydroxy, amino, $(C_1-C_2)$-alkyl, and $(C_1-C_2)$-alkoxy,
    wherein alkyl and alkoxy can be substituted with one up to three substituents selected from the group consisting of $^{76}Br$, $^{75}Br$, $^{19}F$ und $^{18}F$,
  $R_5$, if X represents CH or N, represents a substituent selected from the group consisting of hydrogen, halogen, hydroxy, amino, $(C_1-C_2)$-alkyl, and $(C_1-C_2)$-alkoxy, wherein alkyl and alkoxy can be substituted with one up to three substituents selected from the group consisting of $^{76}Br$, $^{75}Br$, $^{19}F$ and $^{18}F$, $R_5$, if X represents $CH_2$, S or O, represents two substituents independently from one another selected from the group consisting of hydrogen, halogen, hydroxy, amino, $(C_1-C_2)$-alkyl, and $(C_1-C_2)$-alkoxy, wherein alkyl and alkoxy can be substituted with one up to three substituents selected from the group consisting of $^{76}Br$, $^{75}Br$, $^{19}F$ und $^{18}F$, $R_6$, if Y represents CH or N, represents a substituent selected from the group consisting of hydrogen, halogen, hydroxy, amino, $(C_1-C_2)$-alkyl, and $(C_1-C_2)$-alkoxy, wherein alkyl and alkoxy can be substituted with one up to three substituents selected from the group consisting of $^{76}Br$, $^{75}Br$, $^{19}F$ und $^{18}F$, $R_6$, if Y represents $CH_2$, S or O, represents two substituents independently from one another selected from the group consisting of hydrogen, halogen, hydroxy, amino, $(C_1-C_2)$-alkyl, and $(C_1-C_2)$-alkoxy, wherein alkyl and alkoxy can be substituted with one up to three substituents selected from the group consisting of $^{76}Br$, $^{75}Br$, $^{19}F$ und $^{18}F$, wherein the compounds of the formula (I) comprise at least a substituent selected from the group consisting of $^{76}Br$, $^{75}Br$, $^{19}F$ and $^{18}F$, and the salts thereof, the solvates thereof and the solvates of the salts thereof.

A subject matter of the invention are also compounds of the formula (I) in which X and Y independently from one another represent $CH_2$, S or O, wherein X and Y are not simultaneously $CH_2$, $R_1$ and $R_2$ independently from another are selected from the group consisting of $(C_1-C_2)$-alkyl, $(C_1-C_2)$-alkoxy and $(C_1-C_2)$-alkyl sulfonyl, wherein at least one of the residues represented by $R_1$ and $R_2$ is substituted with at least one substituent selected from the group consisting of $^{76}Br$, $^{75}Br$, $^{19}F$ and $^{18}F$, and $R_3$, $R_4$, $R_5$, $R_6$, $R_7$, $R_8$, $R_9$ and $R_{10}$ represent hydrogen, and the salts thereof, the solvates thereof and the solvates of the salts thereof.

A subject matter of the invention also are compounds of the formula (I) selected from the group consisting of:
8-Ethyl-4-(2-fluoroethyl)-3,8,9,10-tetrahydro-2H-bis([1,4]-oxazino)[2,3-b:3',2'-i]phenoxazin-4-ium,
4-(2-Fluoroethyl)-8-(2-hydroxyethyl)-3,8,9,10-tetrahydro-2H-bis([1,4]oxazino)[2,3-b:3',2'-i]phenoxazin-4-ium,
[F-18]-8-Ethyl-4-(2-fluoroethyl)-3,8,9,10-tetrahydro-2H-bis([1,4]-oxazino)[2,3-b:3',2'-i]phenoxazin-4-ium,
[F-18]-4-(2-Fluoroethyl)-8-(2-hydroxyethyl)-3,8,9,10-tetrahydro-2H-bis([1,4]oxazino)[2,3-b:3',2'-i]phenoxazin-4-ium,
[Br-75]-8-Ethyl-4-(2-bromoethyl)-3,8,9,10-tetrahydro-2H-bis([1,4]-oxazino)[2,3-b:3',2'-i]phenoxazin-4-ium,
[Br-75]-4-(2-Bromoethyl)-8-(2-hydroxyethyl)-3,8,9,10-tetrahydro-2H-bis([1,4]oxazino)[2,3-b:3',2'-i]phenoxazin-4-ium,
[Br-76]-8-Ethyl-4-(2-bromoethyl)-3,8,9,10-tetrahydro-2H-bis([1,4]-oxazino)[2,3-b:3,2'-i]phenoxazin-4-ium, and
[Br-76]-4-(2-Bromoethyl)-8-(2-hydroxyethyl)-3,8,9,10-tetrahydro-2H-bis([1,4]oxazino)[2,3-b:3',2'-i]phenoxazin-4-ium,
wherein the respective counterion is freely selectable.

In some embodiments of the invention it can be preferred if the compounds of the formula (I) comprise at least one $^{19}F$ substituent, preferably several $^{19}F$ substituents, such as e.g. two, three, four, five or six.

In some embodiments of the invention it can be preferred if the compounds of the invention comprise at least one substituent, preferably one, two or three substituents selected from $^{76}Br$, $^{75}Br$ or $^{18}F$. In the latter case it can be preferred if two or three substituents are present, that they are identical substituents.

In some embodiments of the invention it can be advantageous if the substituents which are selected from $^{76}Br$, $^{75}Br$, $^{19}F$ and $^{18}F$ are bound to the residues represented by $R_1$ and $R_2$.

A subject matter of the invention is also a method for the production of compounds of the formula (I), wherein a compound of the formula

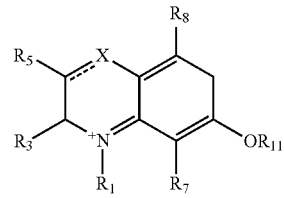

(II)

in which, $R_1$, $R_3$, $R_5$, $R_7$ and $R_8$ have the meaning as defined in claim 1, and $R_{11}$ represents hydrogen, $(C_1-C_4)$-alkyl or phenyl carbonyl, is converted with a compound of the formula

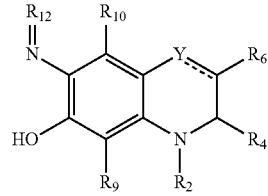

(III)

in which, $R_2$, $R_4$, $R_6$, $R_9$ and $R_{10}$ have the meaning as defined in claim 1, and $R_{12}$ represents oxo or p-nitrophenyl-N.

The conversion in general is realized with a polar solvent in the presence of an acid, preferably in a temperature range of 60° C. until the reflow of the solvent at normal pressure.

Polar solvents are e.g. lower alcohols such as methanol, ethanol, n-propanol or isopropanol, wherein ethanol is preferred.

Acids are preferably mineral acids such as sulfuric acid, nitric acid, hydrochloric acid or bromhydric acid, wherein hydrochloric acid is preferred.

The compounds of the formula (III) can e.g. be produced by converting a compound of the formula (II), wherein $R_{11}$ represents hydrogen, with 4-nitro-phenyl-diazonium-tetrafluorborate.

The reaction is generally realized in a polar solvent in the presence of an acid, preferably at room temperature at normal pressure.

Polar solvents are e.g. lower alcohols such as methanol, ethanol, n-propanol or isopropanol, wherein methanol is preferred.

Acids are preferably mineral acids, in particular diluted mineral acids such as sulfuric acid, nitric acid, hydrochloric acid or hydrobromic acid, wherein diluted sulfuric acid is preferred.

The compounds of the formula (II), in which $R_{11}$ represents hydrogen, can be produced analogously to known methods (see e.g. K.-H. König, *Chem. Berichte*, 1959, 92 (2), 257-267 and A. Y. Berlin, *J. Org. Chem. USSR*, 1958, 2355-2359) from commercially available compounds.

The compounds of the formula (II), in which $R_{11}$ represents $(C_1-C_4)$-alkyl or phenyl carbonyl, can be produced by using common protective groups from compounds of the formula (II), in which $R_{11}$ represents hydrogen.

The $^{76}$Br, $^{75}$Br, $^{19}$F or $^{18}$F substituents being present in the compound according to the invention can already be present in the starting compounds or can be introduced during the synthesis.

In the context of the invention it can be advantageous to synthesize a compound of the formula (II) or (III) in an intermediate stage, in which $R_1$ or $R_2$ represents an hydroxy-$(C_1-C_2)$-alkyl, in a further stage to transfer the hydroxy group of $R_1$ or $R_2$ into a leaving group and then subject it to a nucleophilic substitution reaction for the introduction of a $^{76}$Br, $^{75}$Br, $^{19}$F or $^{18}$F substituent.

The synthesis of the compounds according to the invention can be exemplarily illustrated in the following synthesis scheme.

Reaction scheme 1:

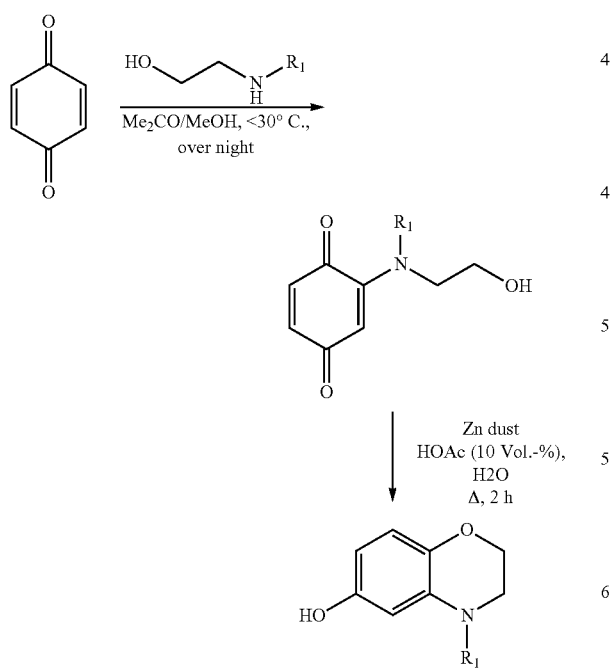

Reaction scheme 2:

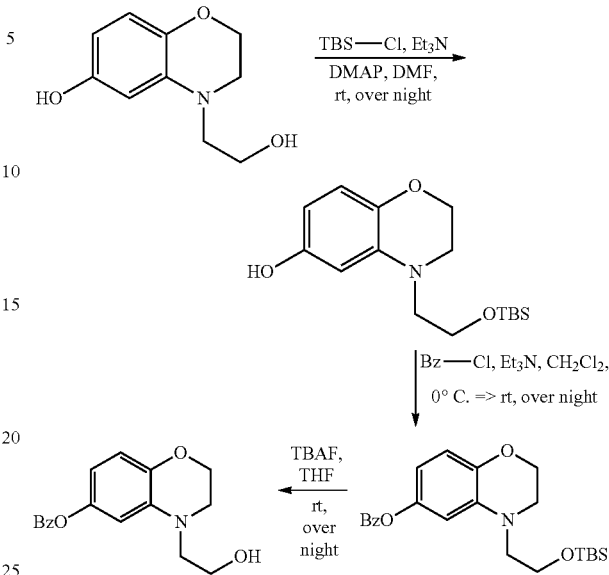

Reaction scheme 3:

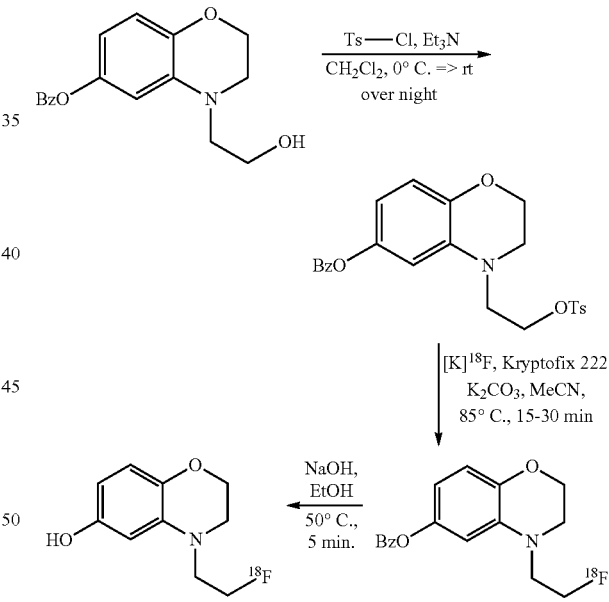

Reaction scheme 4:

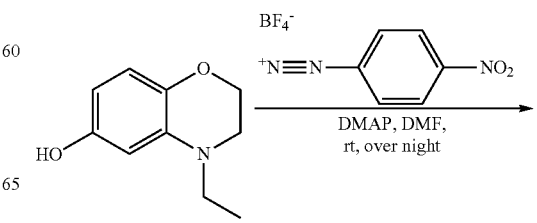

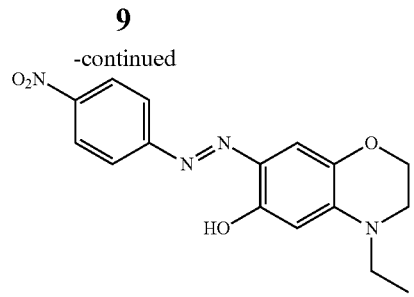

Reaction scheme 5:

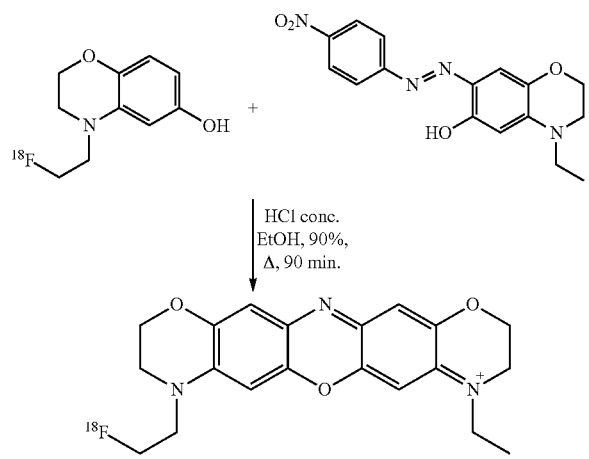

The compounds according to the invention present a non-foreseeable valuable spectrum of activity. The compounds according to the invention show the capability to bind to Aβ plaques wherein the latter can be labeled for a detection by means of an MRT or PET.

For this reason they are suitable for a use as a medicament for the diagnosis of diseases, preferably of dementia diseases and in particular the Alzheimer's disease.

For this reason another subject matter of the present invention is the use of the compounds according to the invention in a method for labeling Aβ plaques.

Another subject matter of the present invention is the use of the compounds according to the invention in a method for the diagnosis of the Alzheimer's disease.

Another subject matter of the present invention is the use of the compounds according to the invention for the production of a medicament for the diagnosis of diseases, preferably of dementia diseases and in particular of the Alzheimer's disease.

Another subject matter of the present invention is a method for the diagnosis of diseases, preferably of dementia diseases and in particular of the Alzheimer's disease, comprising the administration of a compound according to the invention to a human or an animal, which is in need thereof.

Another object of the present invention is a method for labeling Aβ plaques comprising the contacting of a compound according to the invention with biological material, in particular brain parenchyma and brain vasculature.

The before-mentioned method according to the invention can be performed both in vivo, e.g. for the diagnosis of the Alzheimer's disease, but also in vitro, e.g. for the screening of new medicaments.

The compounds according to the invention can be administered systemically and/or locally. Preferably, the compounds according to the invention can be administered parenterally.

For the desired ways of application the compounds according to the invention can be administered in appropriate forms of applications.

The parental application can be realized by circumventing a resorption step (e.g. intravenously, intraarterial, intracardial, intraspinal or intralumbal) or by including a resorption (e.g. intramuscular, subcutaneous, intracutaneous, percutaneous, or intraperitoneal). For the parental application suitable forms of applications are inter alia injection and infusion preparations in the form of solutions, suspensions, emulsions, lyophilisates or sterile powders.

The compounds according to the invention can be converted into the indicated forms of applications. This can be realized in a known manner by mixing with inert, nontoxic, pharmaceutically suitable excipients. These excipients include inter alia vehicles (for example microcrystalline cellulose, lactose, mannitol), solvents (e.g. liquid polyethylene glycols), emulgators and dispersing or wetting agents (for example sodium dodecyl sulfate, polyoxysorbitanoleate), binding agents (for example polyvinylpyrrolidone), synthetic and natural polymers (for example albumin), stabilizers (e.g. antioxidants such as ascorbic acid), dyes (e.g. anorganic pigments such as iron oxides) and flavor and aroma correcting agents.

Another subject matter of the present invention are medicaments which comprise at least a compound according to the invention, usually together with one or several inert, non-toxic pharmaceutically acceptable excipients, and their use for the afore-mentioned purposes.

It is to be understood that the before-mentioned features and those to be mentioned in the following cannot only be used in the combination indicated in the respective case, but also in other combinations or in an isolated manner without departing from the scope of the invention.

The invention is now described and explained in further detail by referring to the following non-limiting examples and drawings. It is shown:

DESCRIPTION OF PREFERRED EMBODIMENTS

Figure 1:
FIG. 1: OI scans of transgenic Alzheimer mice (right) and control animals (left), age 12 months each, after the administration of 0.1 mg/kg body weight of the compound of Example 3, measured 120 min after the injection.

The percentages in the following tests and examples, unless specified otherwise, are % by weight; parts are parts by weight. Solvent ratios, dilution ratios and concentrations of liquid/liquid solutions each refer to the volume.

ABBREVIATIONS

Aβ plaques amyloid beta peptide depositions
Bz-Cl benzoe acid chloride
DMAP 4-dimethylamino pyridine
DMF N,N-dimethylformamide
GC/MS gas chromatography coupled with mass spectrometry
Kryptofix222 4,4,7,13,16,21,24-hexaoxa-1,10-diazabicyclo [8.8.8]-hexacosane
MRT magnet resonance tomography
MW molecular weight
optical imaging
PE petroleum ether or petroleum spirit
PET positron emissions tomography
PIB Pittsburgh compound B
TBAF tetrabutylammonium fluoride trihydrate
TBS-Cl chlor-tert-butyl dimethylsilane
THF tetrahydrofuran
Ts-Cl bzw. Tosyl-chlorid 4-toluolene sulfonic acid chloride A. Analytical Apparatus and Methods GC/MS
Agilent 7890 GC with a 5975C MSD with EI, column: HP5-MS, starting temperature: 50° C., linear temperature gradient to 300° C. within 20 min.
Radio HPLC
Agilent 1260 HPLC with MWD, RI and radio detector.
LC/MS
Agilent 1200 HPLC with MWD and MMI single quad MSD
DC Scanner
Perkin Elmer Cyclone Plus Phosphor Imager.
IR Spectroscopy
Perkin Elmer FT-IR Spectrum ONE with a ATR sampling unit. The samples were either measured in solid or liquid form directly with the ATR sampling unit without the use of pellets or cuvettes.
UV/Vis Spectroscopy
Perkin Elmer Lambda 25 UV/Vis spectrometer. The spectra were recorded in 3 ml quartz glass cuvettes with Uvasol methanol or TraceSelect water as solvent.
Fluorescence Spectroscopy
Perkin Elmer LS 45 fluorescence spectrometer. The spectra were recorded in 3 ml quartz glass cuvettes with Uvasol methanol or TraceSelect water as solvent.

B. Starting Compounds and Intermediates

Example 1A 2-(Ethyl(2-hydroxyethypannino)-1,4-benzochinone

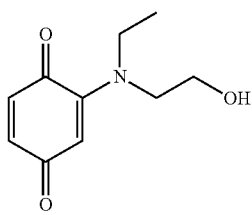

To a solution of 1,4-benzochinone (0.3 mol) in 72 ml acetone at room temperature a solution of 2-(ethylamino) ethanol (0.15 mol) in 18 ml methanol was added in drops in such a way that the temperature of 30° C. was not exceeded. After the complete addition of the methanolic solution the dark brown suspension is stirred over night at room temperature. In the following the suspension is aspirated via a Büchner funnel and the obtained remainder is washed with little ice cold methanol. The yellowish to brown crystals were then dried in an exsiccator over night (yield: 16%).
MW: 181.19 g/mol
GC/MS: m/z=181 (30.8%), 152 (8.5%), 151 (12.3%), 150 (100.0%), 122 (38.5%), 108 (7.3%), 94 (13.3%), 82 (9.2%), 81 (14.8%), 79 (8.1%), 68 (12.5%), 55 (7.7%), 54 (8.2%), 53 (19.9%), 52 (7.4%).

Example 2A 2-(bis(2-Hydroxyethyl)amino)-1,4-benzochinone

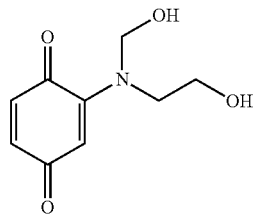 [SMILES: O=C1C=CC(=O)C(N(CO)CCO)=C1]

The synthesis of the title compound is effected analogously to the synthesis of the compound of Example 1A, wherein diethanol amine is used instead of 2-(ethylannino) ethanol. The title compound is obtained in a yield of 77%.
MW: 211.21 g/mol;
GC/MS: m/z=211 (26.8%), 207 (19.6%), 195 (19.6%), 193 (15.0%), 182 (23.1%), 181 (13.7%), 180 (100.0%), 164 (37.7%), 162 (10.2%), 151 (13.4%), 150 (54.0%), 149 (12.7%), 136 (69.4%), 135 (10.1%), 122 (23.3%), 109 (16.(%), 108 (22.1%), 94 (10.(%), 82 (10.3%), 81 (16.7%), 80 (14.0%), 79 (11.2%), 68 (11.1%), 55 (17.6%), 54 (14.3%), 53 (24.5%), 52 (12.8%).

Example 3A

4-Methyl-3,4-dihydro-2H-benzo[b][1,4]oxazin-6-ol

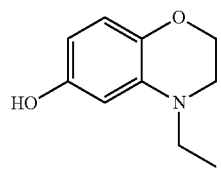

To a solution of the compound of Example 1A (0.1 mol) in 250 ml of 10% acetic acid zinc dust (0.2 mol) is added and the solution is heated for 30 min under reflux until the DC analysis shows a complete reaction conversion. The purple suspension is cooled down to room temperature, filtered through a Büchner funnel and the solid matter is washed with water. The filtrate is neutralized with concentrated ammoniac and for three times extracted with 200 ml ethyl acetate. The pooled organic phases are washed with saturated NaCl solution one time, dried via magnesium sulfate and concentrated in a rotary evaporator, resulting in a dark brown oil (yield: 53%).

MW: 165.19 g/mol

GC/MS: m/z=166 (10.1%), 165 (100.0%), 164 (13.9%), 150 (53.7%), 136 (22.4%), 123 (5.7%), 109 (10.8%), 108 (5.3%), 82 (15.5%), 81 (12.8%), 80 (5.4%), 55 (7.4%), 53 (6.9%).

Example 4A

4-Ethyl-3,4-dihydro-2H-benzo[b][1,4]oxazin-6-ol

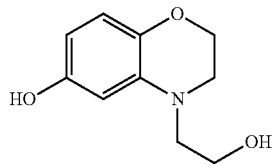

The synthesis of the title compound is effected analogously to the synthesis of the compound of Example 3A, starting from the compound of Example 2A. The title compound is obtained in a yield of 83%.

MW: 179.22 g/mol

GC/MS: m/z=180 (7.4%), 179 (63.1%), 165 (10.8%), 164 (100.0%), 150 (8.1%), 136 (22.5%), 123 (5.4%), 109 (7.7%), 108 (6.8%), 55 (5.1%).

Example 5A 4-(2-(tert-Butyldimethylsilyloxy)ethyl)-3,4-dihydro-2H-benzo[b]-[1,4]-oxazin-6-ol

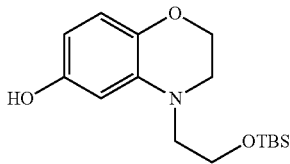 [SMILES: CC(C)(C)[Si](C)(C)OCCN1CCOc2ccc(O)cc21]

To a solution of the compound of Example 4A (27.2 g, 0.139 mol, 1 equ.) in 300 ml DMF at room temperature at first DMAP (~30 mg, cat. amount) and Et$_3$N (29 ml, 0.210 mol, 1.5 equ.) are added. To this solution TBS-Cl (22.03 g, 0.146 mol, 1.05 equ.) is slowly added in portions in solid form, whereby an exothermic reaction can be observed. The obtained reaction solution is stirred at room temperature for 48 hours. For the reprocessing the reaction solution is supplemented with 1.5 l dest. water and the obtained cloudy solution is extracted for four times with 250 ml EtOAc. The pooled organic phases are washed for one time with 300 ml sat. NaCl solution, dried via MgSO$_4$ and concentrated in a rotary evaporator. The obtained remainder is purified by means of column chromatography via silica gel with PE/EtOAc/Et$_3$N=750:250:10 as the eluent, resulting in a dark brown oil (yield: 94%).

MW: 309.48 g/mol

GC/MS: m/z=310 (6.9%), 309 (29.8%), 252 (7.4%), 208 (7.9%), 165 (12.7%), 164 (100.0%), 136 (5.2%), 75 (4.0%), 73 (4.9%).

Example 6A 4-(2-(tert-Butyldimethylsilyloxy)ethyl)-3,4-dihydro-2H-benzo[b][1,4]oxazin-6-yl benzoate

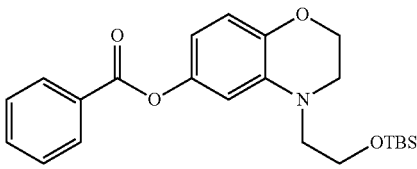 [SMILES: CC(C)(C)[Si](C)(C)OCCN1CCOc2ccc(OC(=O)c3ccccc3)cc21]

To a solution of the compound of Example 5A (10.15 g, 32.8 mmol, 1 equ.) and Et$_3$N (4.8 ml, 34.5 mmol, 1.05 equ.) in 200 ml dichloromethan at 0° C. a 10% solution of benzoyl chloride (4.0 ml, 34.5 mmol, 1.05 equ.) in dichloromethane is slowly added via a dropping funnel. After completing the addition, the reaction solution is maintained in the ice bath and stirred over night with slowly heating up to room temperature. For the reprocessing the brown reaction solution is supplemented with 400 ml dest. water and intensively stirred for 5 min. After the phase separation, the aqueous phase is extracted for three times with 200 ml dichloromethane. The pooled organic phases are then dried via MgSO$_4$ and concentrated in a rotatory evaporator. The remainder is purified by means of a column chromatography via silica gel with PE/EtOAc/Et$_3$N=500:100:5 as the eluent, resulting in a brown oil (yield: ~quant.).

MW: 413.58 g/mol

GC/MS: m/z=324 (5.3%), 323 (22.0%), 266 (4.2%), 222 (3.3%), 179 (12.0%), 178 (100.0%), 150 (4.6%), 135 (2.4%), 75 (2.6%), 73 (3.7%), 59 (2.1%).

Example 7A 4-(2-Hydroxyethyl)-3,4-dihydro-2H-benzo[b][1,4]oxazin-6-yl benzoate

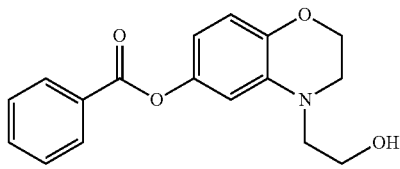 [SMILES: O=C(Oc1ccc2c(c1)N(CCO)CCO2)c1ccccc1]

To a solution of the compound of Example 6A (26.2 mmol, 1 equ.) in 100 ml THF at 0° C. a solution of TBAF (27.5 ml, 27.5 mmol, 1.05 equ., 1M solution in THF) is slowly added and the reaction solution is stirred over night with slowly heating up to room temperature. For the reprocessing the reaction solution is supplemented with 150 ml dest. water and intensively stirred for 5 min. After the phase separation the aqueous solution is for three times extracted with 100 ml of Et$_2$O each. The pooled organic phases are washed for one time with 100 ml of the saturated NaCl solution, dried via MgSO$_4$ and concentrated in a rotary evaporator. The remainder is purified by means of column chromatography via silica gel with PE/EtOAc/Et$_3$N=500:500:5 as the eluent, resulting in a light yellow oil (yield: 72%).

MW: 299.32 g/mol;

GC/MS: m/z=300 (5.0%), 299 (26.8%), 270 (2.2%), 269 (18.0%), 268 (100.0%), 164 (2.9%), 108 (5.6%), 106 (5.1%), 105 (52.7%), 78 (2.2%), 77 (26.4%), 55 (2.3%), 51 (4.8%).

Example 8A 4-(2-Fluoroethyl)-3,4-dihydro-2H-benzo[b][1,4]oxazin-6-yl benzoate

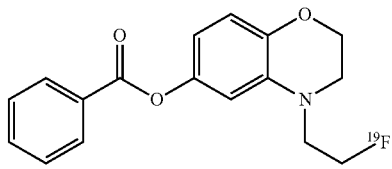

To a solution of the compound of Example 7A (4.49 g, 15 mmol, 1 equ.) in 100 ml THF at room temperature a solution of deoxofluor (13.0 ml, 30 mmol, 2.0 equ., 50% solution in THF) is added and the reaction mixture is stirred at this temperature over night. For the reprocessing the reaction mixture is supplemented with ~50 g of silica gel and concentrated in a rotary evaporator to dryness. The remainder is purified by means of column chromatography via silica gel with PE/EtOAc/Et$_3$N=300:150:5 as the eluent, resulting in a yellow oil (yield: 79%)

MW: 301.31 g/mol

GC/MS: m/z=302 (8.5%), 301 (44.6%), 269 (3.4%), 268 (18.5%), 168 (3.4%), 106 (8.4%), 105 (100.0%), 77 (28.9%), 51 (4.8%).

Example 9A 4-(2-Bromoethyl)-3,4-dihydro-2H-benzo[b][1,4]oxazin-6-yl-benzoate

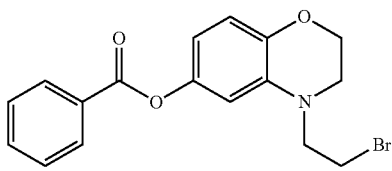 [SMILES: O=C(Oc1ccc2c(c1)N(CCBr)CCO2)c1ccccc1]

To a solution of the compound of Example 7A (1 g, 3.34 mmol, 1 equ.) in 30 ml CHCl$_3$ at room temperature CBr$_4$ (2.23 g, 6.68 mmol, 2.0 equ.) followed by PPh$_3$ (1.75 g, 6.68 mmol, 2.0 equ.) are added and the reaction mixture is stirred at this temperature for 60 min. After a complete conversion of the starting material has been determined by means of DC analysis, the cloudy solution is filtered and supplemented with ~20 g of silica gel. The suspension is concentrated in a rotary evaporator to dryness and the obtained remainder is purified by means of column chromatography via silica gel with PE/EtOAc/Et$_3$N=100:300:5 as the eluent, resulting in a yellow oil (yield ~quant.).

MW: 362.22 g/mol

GC/MS: m/z=364 (4.3%), 363 (23.4%), 362 (4.7%), 361 (23.8%), 282 (2.6%), 269 (7.1%), 268 (39.9%), 109 (3.1%), 108 (3.5%), 107 (4.1%), 106 (8.4%), 105 (100.0%), 78 (2.3%), 77 (28.5%), 51 (4.7%).

Example 10A 4-(2-(Tosyloxy)ethyl)-3,4-dihydro-2H-benzo[b][1,4]oxazin-6-yl-benzoate

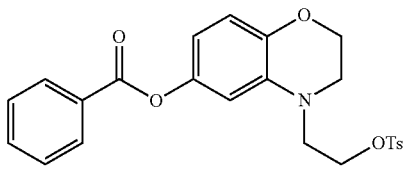 [SMILES: Cc1ccc(S(=O)(=O)OCCN2CCOc3ccc(OC(=O)c4ccccc4)cc32)cc1]

To a solution of the compound of Example 7A (1 g, 3.34 mmol, 1 equ.) and Et$_3$N (0.7 mL, 5.0 mmol, 1.5 equ.) in 30 ml dichloromethane at 0° C. a solution of tosyl chloride (0.7 g, 3.67 mmol, 1.1 equ.) in 10 ml dichloromethane is slowly added in drops. The obtained reaction solution is stirred over night with slowly heating up. For the reprocessing the reaction solution is supplemented with 100 ml water and intensively stirred for 5 min. After the phase separation the aqueous phase is extracted for three times with 75 ml of dichloromethane. The pooled organic phases are washed for one time with 100 ml of a saturated NaCl solution, dried via MgSO$_4$ and concentrated in a rotary evaporator, resulting in a brown oil. The remainder is purified by means of column chromatography via silica gel with PE/EtOAc/Et$_3$N=300:100:5 as the eluent, resulting in a light brown oil, which solidifies when storing in the fridge (yield: 74%).

MW: 453.51 g/mol

GC/MS: m/z=342 (9.6%), 341 (35.7%), 281 (14.7), 269 (16.5%), 268 (100.0%), 208 (6.0%), 207 (25.6%), 148 (4.4%), 135 (4.6%), 108 (6.0%), 106 (8.8%), 105 (84.7%), 87 (8.4%), 78 (4.6%), 77 (27.1%), 73 (8.2%), 51 (4.8%).

Example 11A

[F-18]-4-(2-Fluoroethyl)-3,4-dihydro-2H-benzo[b][1,4]oxazin-6-yl-benzoate

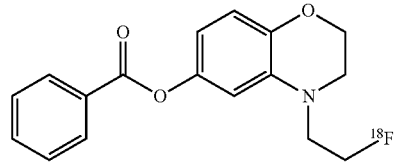 [SMILES: O=C(Oc1ccc2c(c1)N(CC[18F])CCO2)c1ccccc1]

1. Step: Production of the Radioactive Fluoric Reagent

In a 5 ml reaction vessel (reaction vial) 2 ml of aqueous H$^{18}$F is deposited and at room temperature supplemented with 100 μl of a 3.5% of aqueous potassium carbonate solution, 16 mg of Kryptofix222 (Merck Darmstadt) and 1 ml acetonitrile (DNA grade). The solution is heated to 140° C. with intensive stirring in an argon gas stream. In intervals of 4 min 1 ml of acetonitrile each are added. 20 min after the reaction start it is verified whether there is still liquid present in the reaction vessel. If liquid is still present, the reaction mixture is stirred for additional 4 min. In the following the reaction vessel is cooled down to −30° C. and the remainder is dissolved into 1 ml acetonitrile, resulting in a yellow solution. This solution is then directly used for the radio labeling in the next step.

2. Step: Radio Labeling

To a solution of the compound of Example 10A (4 mg) in 1 ml of abs. acetonitrile the solution of [K]$^{18}$F prepared in step 1 is added and the obtained reaction mixture is stirred at 85° C. for 30 min. After cooling down to −30° C. the reaction mixture is put onto a preparative HPLC (column: Phenomenex Luna C18(2), 250×10 mm, eluent: 60% acetonitrile/40% water, flow rate: 7 ml/min, detector: UV and radio activity) and the product is separated from the starting material. The product fraction is diluted with 70 ml of dest. water and put onto a conditioned Strata-X-SPE cartridge (Phenomenex, 10 mg bed material), whereby the radiolabeled product is retained on the bed material. In the following the Strata-X cartridge is washed with 5 ml water and the excessive water is removed with 5 ml of air. Finally, the product is eluated with 1 ml of 96% ethanol from the cartridge (yield: 22%).

Die identification of the title compound is realized via radio-DC with PE/EtO$_2$ as the eluent.

Example 12A 4-(2-Fluoroethyl)-3,4-dihydro-2H-benzo[b][1,4]oxazin-6-ol

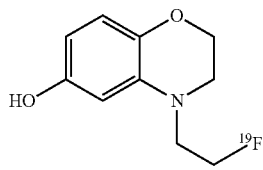 [SMILES: Oc1ccc2c(c1)N(CCBr)CCO2]

To a solution of the compound of Example 8A (2 mmol, 1 equ.) in 30 ml of abs. methanol solid caustic soda (MW: 40.0 g/mol, 84 mg, 2.1 mmol, 1.05 eq.) is added and the reaction mixture is stirred at room temperature over night. For the reprocessing the reaction solution is supplemented with ~25 g of silica gel and concentrated in a rotary evaporator to dryness. The remainder is separated by means of column chromatography via silica gel (eluent: PE/EtOAc/Et$_3$N=400:600:5), resulting in an oil (yield: 99%).

MW: 197.21 g/mol;
GC/MS: m/z=198 (10.4%), 197 (79.6%), 168 (4.9%), 165 (16.2%), 164 (100.0%), 136 (29.2%), 123 (7.4%), 109 (12.0%), 108 (10.4%), 94 (4.3%), 82 (6.7%), 81 (5.7%), 65 (4.4%), 55 (5.2%), 53 (5.6%);

Example 13A 4-(2-Bromoethyl)-3,4-dihydro-2H-benzo[b][1,4]oxazin-6-ol

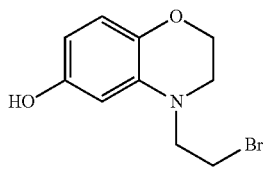

Die synthesis of the title compound is realized analogously to the synthesis of the compound of Example 12A, starting from the compound of Example 9A, whereby for the purification PE/EtOAc/Et$_3$N=700:300:25 is used as the eluent. The title compound is obtained in a yield of >90%.

The title compound is instable and decomposes within 12 hours to 50% at −25° C. For this reason the title compound is further converted directly after the isolation.

MW: 258.11 g/mol;
GC/MS: m/z=259 (20.7%), 257 (18.7%), 207 (4.4%), 178 (5.5%), 165 (11.7%), 164 (100.0%), 148 (3.9%), 136 (12.8%), 123 (4.4%), 109 (6.9%), 108 (4.6%), 94 (3.7%), 82 (4.3%), 55 (3.5%).

Example 14A

4-Ethyl-7-((4-nitrophenyl)diazenyl)-3,4-dihydro-2H-benzo[b][1,4]oxazin-6-ol

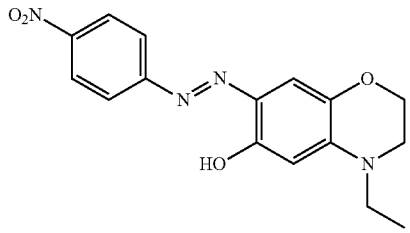 [SMILES: CCN1CCOc2cc(/N=N/c3ccc([N+](=O)[O-])cc3)c(O)cc21]

To a solution of the compound of Example 3A (3 mmol, 1 equ.) in 10 ml methanol at room temperature a solution of 4-nitro-phenyl-diazonium-tetrafluoroborate (710 mg, 3 mmol, 1 equ.) in 2 ml of 10% aqueous sulfuric acid is added. The dark red reaction solution is stirred for 30 min at room temperature and neutralized by half concentrated ammonia solution. The obtained red precipitate is filtered and washed on the filter with cold dest. water. In the following the red solid matter is dried in an oil pump vacuum over night and recrystallized from n-butanol (yield: 82%).

MW: 328.32 g/mol;
LC/MS: m/z=330 (19.3%), 329 (100.0%);

Example 15A 4-(2-Hydroxyethyl)-7-((4-nitrophenyl)diazenyl)-3,4-dihydro-2H-benzo[b][1,4]-oxazin-6-ol

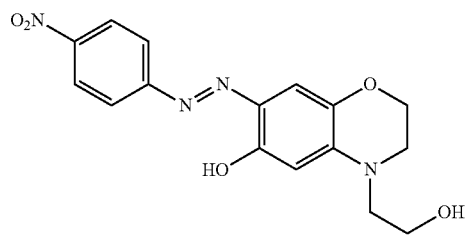 [SMILES: O=[N+]([O-])c1ccc(/N=N/c2cc3c(cc2O)N(CCO)CCO3)cc1]

The synthesis of the title compound is realized analogously to the synthesis of the compound of Example 14A, starting from the compound of Example 4A. The title compound is obtained in a yield of 94%.

MW: 344.32 g/mol;
LC/MS: m/z=346 (19.0%), 345 (100.0%);

C. Exemplary Compounds

Example 1

8-Ethyl-4-(2-fluoroethyl)-3,8,9,10-tetrahydro-2H-bis([1,4]oxazino)[2,3-b:3',2'-i]phenoxazin-4-ium chloride

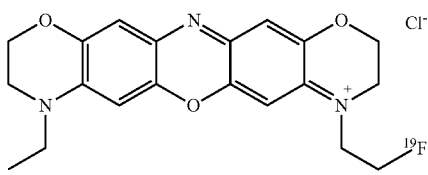

To a solution of the compound of Example 14A (2 mmol, 1 equ.) and of the compound of Example 12A (3 mmol, 1.5 equ.) in 12 ml of 90% ethanol 1 ml of 32% hydrochloric acid is added and the reaction solution is heated for 60-240 min under reflux (~80° C.) until the DC or LC/MS analysis shows a complete reaction conversion. For the reprocessing the reaction solution is neutralized with concentrated ammonia solution and concentrated in a rotary evaporator to dryness. The obtained remainder is dissolved in methanol, supplemented with ~10 g silica gel and again concentrated in the rotary evaporator to dryness. The green blue remainder is purified by means of column chromatography via silica gel with $CH_2Cl_2$/MeOH=20:1 as the eluent, resulting in a greenish to blue solid matter (yield: 62%).

MW: 405.85 g/mol

LC/MS: m/z=371 (22.9%), 370 (100.0%).

Example 2

4-(2-Bromoethyl)-8-ethyl-3,8,9,10-tetrahydro-2H-bis([1,4]oxazino)[2,3-b:3',2'-i]phenoxazin-4-ium bromide

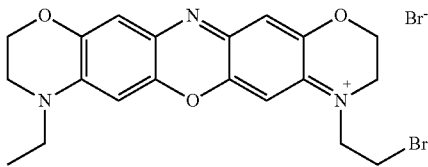

The synthesis of the title compound is realized analogously to the synthesis of the compound of Example 1, starting from the compounds of Example 14A and Example 13A. After the purification of the raw product by means of column chromatography with silica gel and $CH_2Cl_2$/MeOH=1000:50 as the eluent the title compound is obtained in a yield of 24%.

This compound does not fall under the scope of protection of claim 1 and merely serves as a non-radioactive model compound for $^{76}Br$ and $^{75}Br$ substituted compounds.

MW: 511.12 g/mol

LC/MS: m/z=436 (13.8%), 435 (46.4%), 434 (19.8%), 433 (57.0%), 247 (15.0%), 231 (10.1%), 230 (13.3%), 213 (13.7%), 207 (10.2%), 166 (100.0%), 138 (21.5%), 137 (65.1%), 125 (16.0%), 124 (49.5%);

Example 3

[F-18]-8-Ethyl-4-(2-Fluoroethyl)-3,8,9,10-tetrahydro-2H-bis([1,4]-oxazino)[2,3-b:3',2'-i]phenoxazin-4-ium chloride

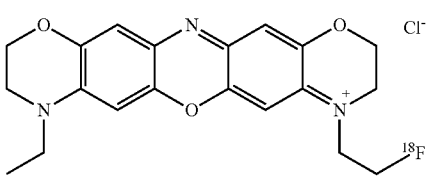

To an ethanolic solution of the compound of Example 11A at room temperature 2 mg of solid caustic soda are added and the reaction mixture is stirred at 50° C. for 5 min, whereby a complete conversion is observed by means of radio DC. To this reaction solution a solution consisting of the compound of Example 14A (4 mg) and 50 µl of concentrated hydrochloric acid are added and the reaction mixture is stirred at 75° C. for 20 min. The reaction mixture is purified by HPLC and the title compound is obtained in a yield of 8%.

The identification of the title compound is realized via radio DC with $CH_2Cl_2$/MeOH 10:1 as the eluent and radio HPLC with the compound of Example 1 as the reference substance.

Example 4

4-(2-Fluoroethyl)-8-(2-hydroxyethyl)-3,8,9,10-tetrahydro-2H-bis([1,4]oxazino)[2,3-b:3',2'-i]phenoxazin-4-ium chloride

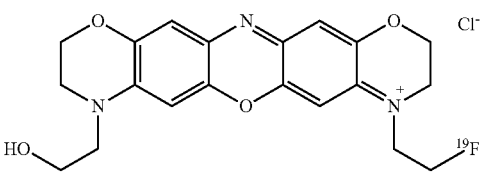

The synthesis of the title compound is realized analogously to the synthesis of the compound of Example 1, starting from the compounds of Example 15A and Example 12A. After the purification of the raw product by column chromatography with silica gel and a gradient of $CH_2Cl_2$/MeOH=20:1 to $CH_2Cl_2$/MeOH=1:1 the title compound is obtained in a yield of 24%.

MW: 421.85 g/mol

LC/MS: m/z=388 (7.6%), 387 (29.0%), 386 (100.0%), 385 (6.0%).

D. Evaluation of the Physiological Activity

Detection of Aβ Plaques by Means of Optical Imaging (OI) in the Mouse Model

To demonstrate the selective labeling of Aβ plaques by radioactively labeled compounds of the invention and of the imaging of the labeling by OI, transgenic APPPS1 mice and non-transgenic control mice of different age (provided by Prof. Mathias Jucker, Department of Cellular Neurology, Hertie-Institute for Clinical Brain Research, University of Tubingen) were treated with 0.1 mg/kg body weight of the compound of Example 3 and then examined by means of OI. The compound was formulated in physiological saline solution (0.9% NaCl) in a concentration of 0.05 mg/ml and intravenously injected into the mice. In the following the mice were examined by means of OI (Aequoria Hamamatsu Optical Imaging System), the signal was detected at 650 nm.

The experiments are intended to demonstrate the general capability of the compounds according to the invention to bind to Aβ plaques and to provide a signal correlating with the concentration of Aβ plaques. It is clear for the skilled person that this labeling can—depending on the kind of labeling—be realized by any method, such as OI, PET (e.g. with $^{76}$Br, $^{75}$Br or $^{18}$F labeled compounds) or MRT (e.g. with $^{19}$F labeled compounds).

These experiments have shown that the compound of Example 3 specifically accumulates in transgenic mice wherein in the control mice no accumulation could be detected (see FIG. 1).

Figure 2:
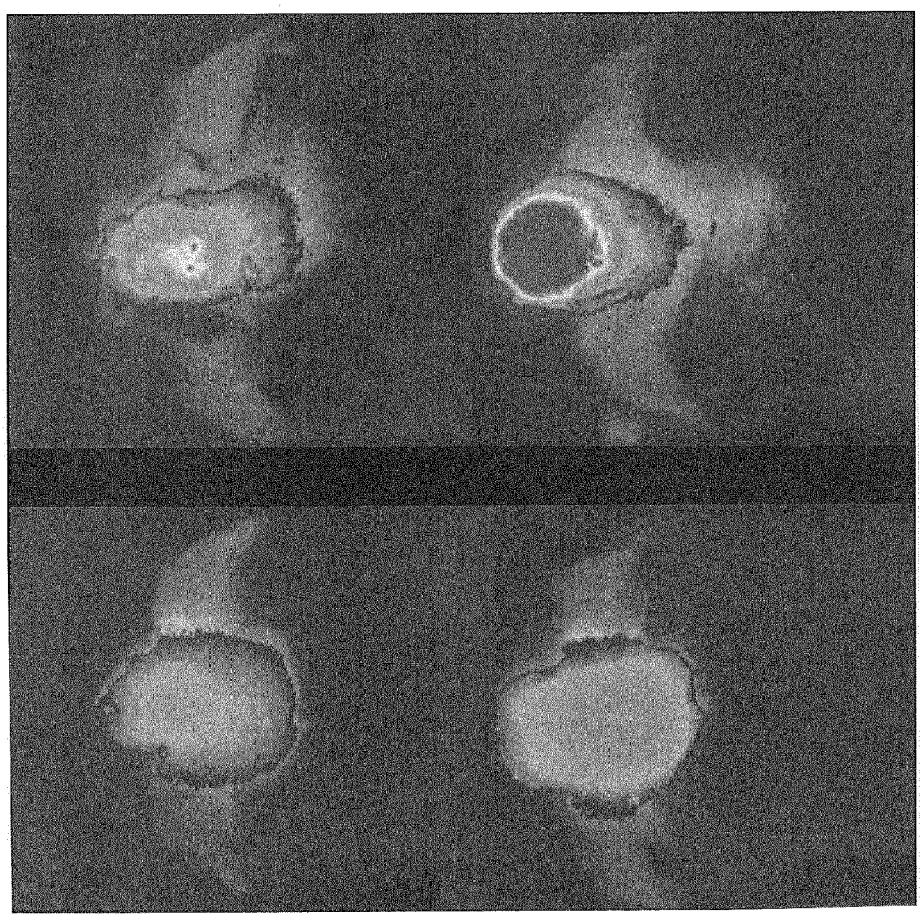
FIG. 2: OI scans of transgenic Alzheimer mice (right) and control animals (left) after the administration of 0.1 mg/kg body weight of the compound of Example 3, for animals at the age of 2 months (top row) and 12 months (low row)

It has further been shown that the enrichment of the compound of Example 3 increases with the age of the transgenic mice and hence with the increasing formulation of Aβ plaques. It can be seen that in transgenic mice of an age of 2 months where Aβ plaques rarely have been formed no enrichment can be detected, whereas at the age of 12 months a significant enrichment can be seen (see FIG. 2).

Figure 3:
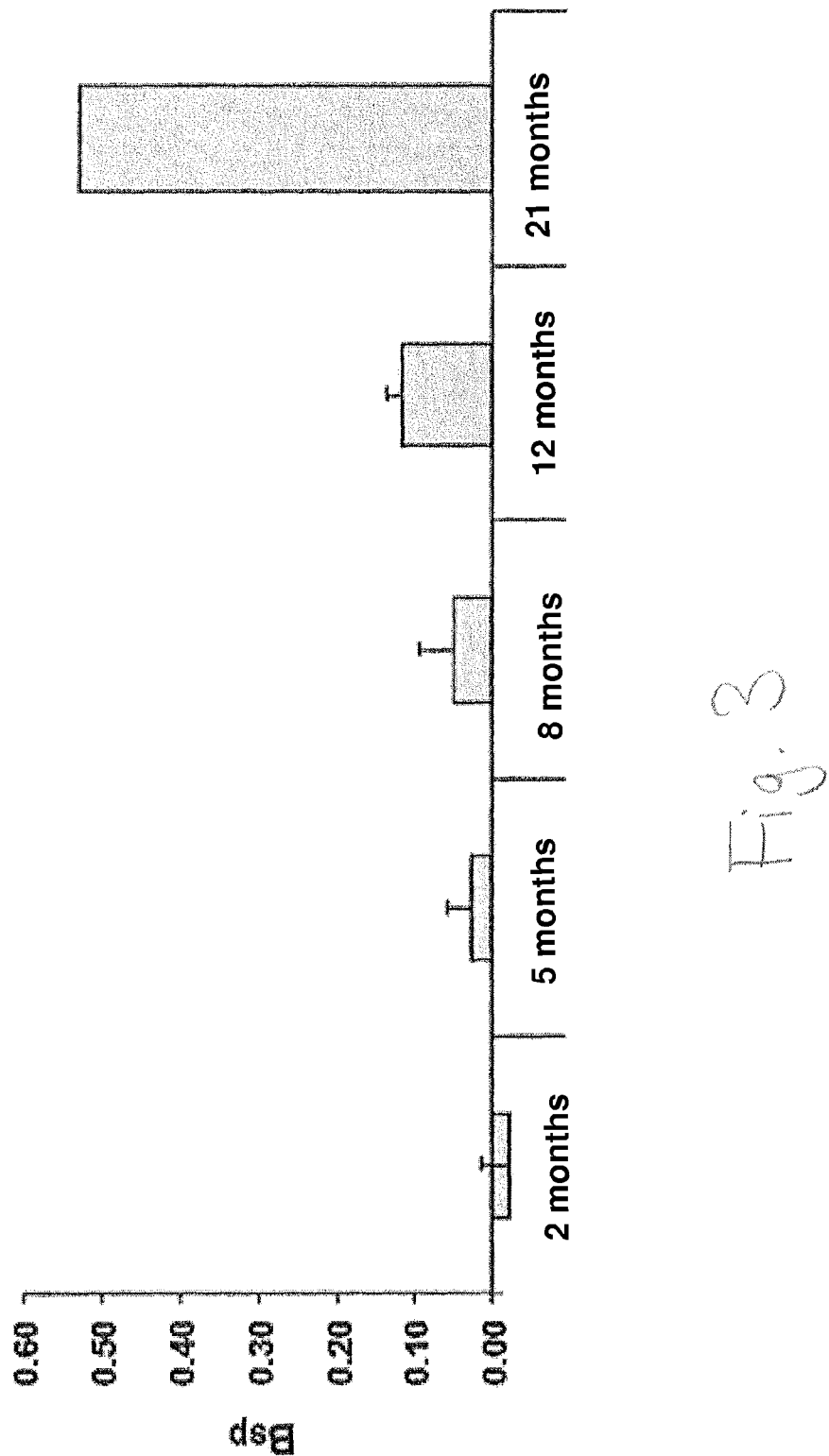
FIG. 3: a diagram where the signals measured in OI scans for the accumulation of the compound of Example 3 are plotted against the age of transgenic Alzheimer mice.

The signal strength was quantified as a relative fluorescence signal, whereby 30 min after the injection was chosen as the reference point in time. The signal strength was calculated by percentage after the subtraction of the auto fluorescence (resulting in relative intensity values, $I_{rel}$) and then the percentage difference between the transgenic and control mice—in the following referred to as specific binding ($B_{sp}$)—was calculated and plotted against the age of the transgenic mice (see FIG. 3). It turned out that there is a significant correlation between the age and the development of the Alzheimer's disease and the signal strength, where it was especially noted that the compound according to the invention has no saturation or ceiling effects in a way that the signal strength is not increasing at a specific concentration of Aβ plaques. To the contrary, at the age of 21 months for the transgenic mice a particularly strong signal has been measured.

Detection of Aβ Plaques by Means of MRT in the Mice Model

For the demonstration of the selective labeling of Aβ plaques by the fluor labeled compounds of the invention and the imaging of the labeling by MRT, trangenic APP23 mice and non-transgenic control mice (provided by Dr. Matthias Staufenbiel, Novartis Institutes for BioMedical Research, Basel, Switzerland) at the age of 28 months were treated with 2 mg/kg body weight of the compound of Example 1 (the compound was formulated in physiological saline solution (0.9% NaCl) in a concentration of 1 mg/ml) and then examined by means of MRT (ClinScan, Bruker BioSpin MRI, Ettlingen, Germany) and analyzed by optical fluorescence measurements (Aequoria Hamamatsu Optical Imaging System) and evaluated as described before. For the MRT measurements a threedimensional gradient echosequence (gre3D) which both comprises T1 as well as T2* parts, and a quantitative T2 value determination sequence (T2map) were used. By doing so, again a specific enrichment in the transgenic mice could be detected over the measurement time period of 90 minutes. In the control mice neither for the MRT measurements nor the fluorescence measurements a specific enrichment of the compound of Example 1 could be observed.

Figure 4:
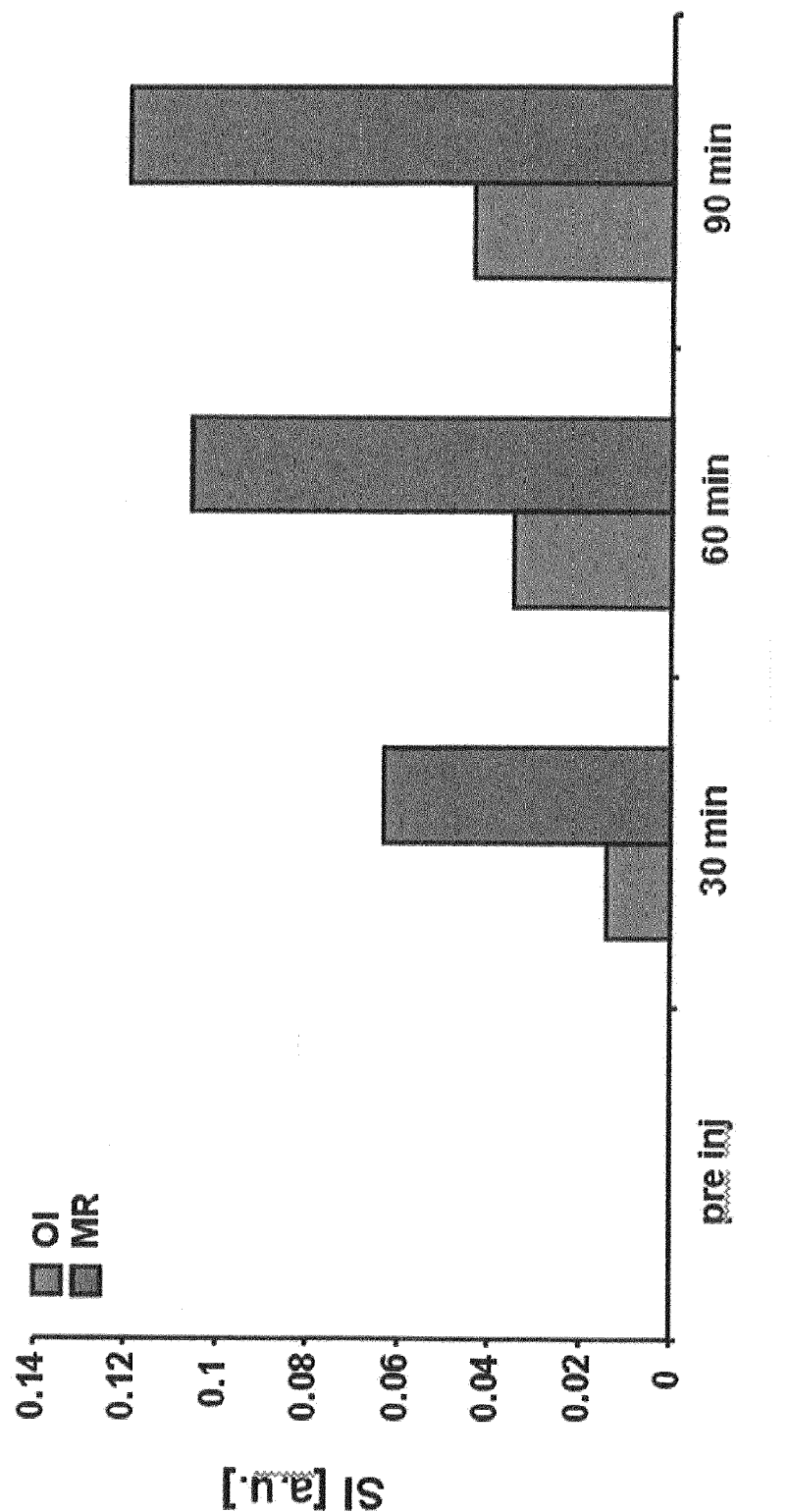
FIG. 4: a diagram where the signals measured in MRT scans for the accumulation of the compound of Example 1 and signals of corresponding measurements of the fluorescence are plotted against the measurement period.

The values obtained from the MRT were compared with the values of the fluorescence measurement resulting in a significant correlation as can be seen in the diagram of FIG. 4. The observations made in vivo could also be confirmed ex vivo after a preparation of the brains.

Summary

With these experiments the suitability of the compounds according to the invention for the labeling in vivo of Aβ plaques and their non-invasive detection could be demonstrated by OI as well as by MRT. It has been shown that the compounds according to the invention bind to Aβ plaques with high selectivity and provide a signal correlating with the concentration of Aβ plaques over a wide concentration range. It results from the OI examinations by using the compound of Example 3 that this compound selectively binds to Aβ plaques, where it is clear to the skilled person that this compound, due to the presence of $^{18}$F, is also suitable for the analysis by PET and will provide analogous results. The compounds according to the invention are therefore excellently suited for the non-invasive diagnosis of the Alzheimer's disease and the monitoring of the process of the disease.

Therefore, what claimed is:

1. Radioactive tracer of the formula

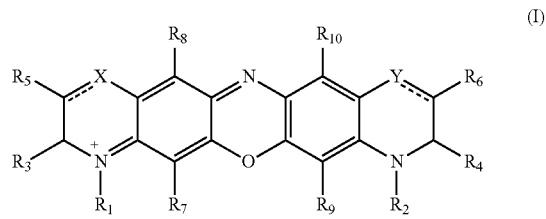

in which,
X and Y independently from one another represent CH, $CH_2$, N, S or O,
wherein X and Y are not simultaneously CH or $CH_2$,
wherein, if X represents CH or N, the dotted line between X and the neighboring atom represents a bond, and
wherein, if Y represents CH or N, the dotted line between Y and the neighboring atom represents a bond,
$R_1$ and $R_2$ independently from one another are selected from the group consisting of ($C_1$-$C_2$)-alkyl, ($C_1$-$C_2$)-alkoxy and ($C_1$-$C_2$)-alkyl sulfonyl,
wherein alkyl, alkoxy and alkyl sulfonyl can be substituted with one up to three substituents selected from the group consisting of $^{76}$Br, $^{75}$Br, $^{19}$F and $^{18}$F,
$R_3$, $R_4$, $R_7$, $R_8$, $R_9$ and $R_{10}$ independently from one another are selected from the group consisting of hydrogen, halogen, hydroxy, amino, cyano, nitro, ($C_1$-$C_4$)-alkyl, ($C_1$-$C_4$)-alkyl amino and ($C_1$-$C_4$)-alkoxy,
wherein alkyl and alkoxy can be substituted with one up to three substituents selected from group consisting of $^{76}$Br, $^{75}$Br, $^{19}$F and $^{18}$F,
$R_5$, if X represents CH or N, represents a substituent selected from the group consisting of hydrogen, halogen, hydroxy, amino, cyano, nitro, ($C_1$-$C_4$)-alkyl, ($C_1$-$C_4$)-alkyl amino and ($C_1$-$C_4$)-alkoxy, wherein alkyl and alkoxy can be substituted with one up to three substituents selected from group consisting of $^{76}Br$, $^{75}Br$, $^{19}F$ and $^{18}F$, $R_5$, if X represents $CH_2$, S or O, represents two substituents independently from one another selected from the group consisting of hydrogen, halogen, hydroxy, amino, cyano, nitro, $(C_1-C_4)$-alkyl, $(C_1-C_4)$-alkyl amino and $(C_1-C_4)$-alkoxy, wherein alkyl and alkoxy can be substituted with one up to three substituents selected from group consisting of $^{76}Br$, $^{75}Br$, $^{19}F$ and $^{18}F$, $R_6$, if X represents CH or N, represents a substituent selected from the group consisting of hydrogen, halogen, hydroxy, amino, cyano, nitro, $(C1-C_4)$-alkyl, $(C_1-C_4)$-alkyl amino and $(C_1-C_4)$-alkoxy, wherein alkyl and alkoxy can be substituted with one up to three substituents selected from group consisting of $^{76}Br$, $^{75}Br$, $^{19}F$ and $^{18}F$, $R_6$, if Y represents $CH_2$, S or O, represents two substituents independently from one another selected from the group consisting of hydrogen, halogen, hydroxy, amino, cyano, nitro, $(C_1-C_4)$-alkyl, $(C_1-C_4)$-alkyl amino and $(C_1-C_4)$-alkoxy, wherein alkyl and alkoxy can be substituted with one up to three substituents selected from group consisting of $^{76}Br$, $^{75}Br$, $^{19}F$ and $^{18}F$, wherein the radioactive tracer of the formula (I) comprises at least one substituent selected from the group consisting of $^{76}Br$, $^{75}Br$, $^{19}F$ and $^{18}F$, and the salts thereof, the solvates thereof and the solvates of the salts thereof.

2. Radioactive tracer of claim 1, wherein

X and Y independently from one another represent CH, $CH_2$, N, S or O, wherein X and Y are not simultaneously CH or $CH_2$, wherein, if X represents CH or N, the dotted line between X and the neighboring atom represents a bond, and wherein, if Y represents CH or N, the dotted line between Y and the neighboring atom represents a bond, $R_1$ and $R_2$ independently from one another are selected from the group consisting of $(C_1-C_2)$-alkyl, $(C_1-C_2)$-alkoxy and $(C_1-C_2)$-alkyl sulfonyl, wherein alkyl, alkoxy and alkyl sulfonyl can be substituted with one up to three substituents selected from the group consisting of $^{76}Br$, $^{75}Br$, $^{19}F$ and $^{18}F$, $R_3$, $R_4$, $R_7$, $R_8$, $R_9$ and $R_{10}$ independently from one another are selected from the group consisting of hydrogen, halogen, hydroxy, amino, $(C_1-C_2)$-alkyl, and $(C_1-C_2)$-alkoxy, wherein alkyl and alkoxy can be substituted with one up to three substituents selected from the group consisting of $^{76}Br$, $^{75}Br$, $^{19}F$ and ad $^{18}F$, $R_5$, if X represents CH or N, represents a substituent selected from the group consisting of hydrogen, halogen, hydroxy, amino, $(C_1-C_2)$-alkyl, and $(C_1-C_2)$-alkoxy, wherein alkyl and alkoxy can be substituted with one up to three substituents selected from the group consisting of $^{76}Br$, $^{75}Br$, $^{19}F$ and $^{18}F$, $R_5$, if X represents $CH_2$, S or O, represents two substituents independently from one another selected from the group consisting of hydrogen, halogen, hydroxy, amino, $(C_1-C_2)$-alkyl, and $(C_1-C_2)$-alkoxy, wherein alkyl and alkoxy can be substituted with one up to three substituents selected from the group consisting of $^{76}Br$, $^{75}Br$, $^{19}F$ and $^{18}F$, $R_6$, if Y represents CH or N, represents a substituent selected from the group consisting of hydrogen, halogen, hydroxy, amino, $(C_1-C_2)$-alkyl, and $(C_1-C_2)$-alkoxy, wherein alkyl and alkoxy can be substituted with one up to three substituents selected from the group consisting of $^{76}Br$, $^{75}Br$, $^{19}F$ and $^{18}F$, $R_6$, if Y represents $CH_2$, S or O, represents two substituents independently from one another selected from the group consisting of hydrogen, halogen, hydroxy, amino, $(C_1-C_2)$-alkyl, and $(C_1-C_2)$-alkoxy, wherein alkyl and alkoxy can be substituted with one up to three substituents selected from the group consisting of $^{76}Br$, $^{75}Br$, $^{19}F$ and $^{18}F$, wherein the radioactive tracer of the formula (I) comprises at least a substituent selected from the group consisting of $^{76}Br$, $^{75}Br$, $^{19}F$ and $^{18}F$, and the salts thereof, the solvates thereof and the solvates of the salts thereof.

3. Radioactive tracer of claim 2, wherein

X and Y independently from one another represent $CH_2$, S or O, wherein X and Y are not simultaneously $CH_2$, $R_1$ and $R_2$ are independently from another selected from the group consisting of $(C_1-C_2)$-alkyl, $(C_1-C_2)$-alkoxy and $(C_1-C_2)$-alkyl sulfonyl, wherein at least one of the residues represented by $R_1$ and $R_2$ is substituted with at least one substituent selected from the group consisting of $^{76}Br$, $^{75}Br$, $^{19}F$ and $^{19}F$, and $R_3$, $R_4$, $R_5$, $R_6$, $R_7$, $R_8$, $R_9$ and $R_{10}$ represent hydrogen, and the salts thereof, the solvates thereof and the solvates of the salts thereof.

4. Medicament comprising at least one radioactive tracer in combination with at least one inert non-toxic pharmaceutical acceptable excipient, said radioactive tracer is of claim 3.

5. Medicament comprising at least one radioactive tracer in combination with at least one inert non-toxic pharmaceutical acceptable excipient, said radioactive tracer is of claim 2.

6. Radioactive tracer of claim 1, wherein

X and Y independently from one another represent $CH_2$, S or O, wherein X and Y are not simultaneously $CH_2$, $R_1$ and $R_2$ are independently from another selected from the group consisting of $(C_1-C_2)$-alkyl, $(C_1-C_2)$-alkoxy and $(C_1-C_2)$-alkyl sulfonyl, wherein at least one of the residues represented by $R_1$ and $R_2$ is substituted with at least one substituent selected from the group consisting of $^{76}Br$, $^{75}Br$, $^{19}F$ and $^{18}F$, and $R_3$, $R_4$, $R_5$, $R_6$, $R_7$, $R_8$, $R_9$ and $R_{10}$ represent hydrogen, and the salts thereof, the solvates thereof and the solvates of the salts thereof.

7. Medicament comprising at least one radioactive tracer in combination with at least one inert non-toxic pharmaceutical acceptable excipient, said radioactive tracer is of claim 6.

8. Radioactive tracer of claim 1, selected from the group consisting of:

8-Ethyl-4-(2-fluoroethyl)-3,8,9,10-tetrahydro-2H-bis([1,4]-oxazino)[2,3-b:3',2'-i]phenoxazin-4-ium, 4-(2-Fluoroethyl)-8-(2-hydroxyethyl)-3,8,9,10-tetra-hydro-2H-bis([1,4]oxazino)[2,3-b:3',2'-i]phenoxazin-4-ium,

[F-18]-8-Ethyl-4-(2-fluoroethyl)-3,8,9,10-tetrahydro-2H-bis([1,4]-oxazino)[2,3-b:3',2'-i]phenoxazin-4-ium,

[F-18]-4-(2-Fluoroethyl)-8-(2-hydroxyethyl)-3,8,9,10-tetrahydro-2H-bis([1,4]oxazino)[2,3-b:3',2'-i]phenoxazin-4-ium,

[Br-75]-8-Ethyl-4-(2-bromoethyl)-3,8,9,10-tetrahydro-2H-bis([1,4]-oxazino)[2,3-b:3',2'-i]phenoxazin-4-ium,

[Br-75]-4-(2-Bromoethyl)-8-(2-hydroxyethyl)-3,8,9,10-tetrahydro-2H-bis([1,4]oxazino)[2,3-b:3',2'-i]phenoxazin-4-ium,

[Br-76]-8-Ethyl-4-(2-bromoethyl)-3,8,9,10-tetrahydro-2H-bis([1,4]-oxazino)[2,3-b:3',2'-i]phenoxazin-4-ium, und

[Br-76]-4-(2-Bromoethyl)-8-(2-hydroxyethyl)-3,8,9,10-tetrahydro-2H-bis([1,4]oxazino)[2,3-b:3',2'-i]phenoxazin-4-ium, wherein the respective counterion is freely selectable.

9. Medicament comprising at least one radioactive tracer in combination with at least one inert non-toxic pharmaceutical acceptable excipient, said radioactive tracer is of claim 8.

10. Radioactive tracer of the formula (I) of claim 1 for a use in a method for diagnosing the Alzheimer's disease.

11. Medicament comprising at least one radioactive tracer in combination with at least one inert non-toxic pharmaceutical acceptable excipient, said radioactive tracer is of claim 1.

12. Medicament of claim 11 for a use in a method for the diagnosis of the Alzheimer's disease.

13. Method for the diagnosis of diseases in humans and animals, comprising the administration of a medicament of claim 11 to a human or animal in need thereof.

14. Method of claim 13, wherein said diseases are dementia diseases.

15. Method of claim 13, wherein said diseases are the Alzheimer's disease.

* * * * *